United States Patent
Sa et al.

(10) Patent No.: US 9,498,773 B2
(45) Date of Patent: *Nov. 22, 2016

(54) CATALYST SYSTEM FOR OLEFIN OLIGOMERIZATION, AND METHOD FOR OLEFIN OLIGOMERIZATION USING THE SAME

(71) Applicant: LG CHEM, LTD., Seoul (KR)

(72) Inventors: Seok Pil Sa, Daejeon (KR); Yong Ho Lee, Daejeon (KR); Ki Soo Lee, Daejeon (KR); Eun Ji Shin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/760,158

(22) PCT Filed: Nov. 18, 2014

(86) PCT No.: PCT/KR2014/011078
§ 371 (c)(1),
(2) Date: Jul. 9, 2015

(87) PCT Pub. No.: WO2015/072812
PCT Pub. Date: May 21, 2015

(65) Prior Publication Data
US 2016/0045906 A1    Feb. 18, 2016

(30) Foreign Application Priority Data

Nov. 18, 2013 (KR) .................. 10-2013-0139995
Nov. 17, 2014 (KR) .................. 10-2014-0160180

(51) Int. Cl.
| | | |
|---|---|---|
| B01J 31/34 | (2006.01) | |
| B01J 31/18 | (2006.01) | |
| C07F 9/46 | (2006.01) | |
| B01J 31/00 | (2006.01) | |
| C07C 2/32 | (2006.01) | |
| C07C 2/36 | (2006.01) | |
| B01J 31/14 | (2006.01) | |
| C07F 9/50 | (2006.01) | |
| B01J 31/24 | (2006.01) | |

(52) U.S. Cl.
CPC ............ *B01J 31/186* (2013.01); *B01J 31/00* (2013.01); *B01J 31/143* (2013.01); *C07C 2/32* (2013.01); *C07C 2/36* (2013.01); *C07F 9/46* (2013.01); *C07F 9/5027* (2013.01); *B01J 31/2414* (2013.01); *B01J 31/34* (2013.01); *B01J 2231/20* (2013.01); *B01J 2531/62* (2013.01); *C07C 2531/14* (2013.01); *C07C 2531/18* (2013.01); *C07C 2531/22* (2013.01); *C07C 2531/24* (2013.01)

(58) Field of Classification Search
CPC ............ C08F 4/69034; C08F 4/60013; C08F 4/78; C07F 9/50; C07F 9/5022; C07C 2/06; C07C 2/08; B01J 31/2414; B01J 31/2409; B01J 31/34; B01J 2231/20
See application file for complete search history.

(56) References Cited

U.S. PATENT DOCUMENTS

| | | | | |
|---|---|---|---|---|
| 7,259,123 | B2 * | 8/2007 | De Boer | B01J 31/188 502/103 |
| 7,378,537 | B2 * | 5/2008 | Small | B01J 31/143 502/113 |
| 8,076,523 | B2 | 12/2011 | Bollmann et al. | |
| 2007/0232481 | A1 | 10/2007 | Zhang et al. | |
| 2012/0172645 | A1 * | 7/2012 | Sydora | B01J 31/143 585/511 |
| 2012/0310025 | A1 | 12/2012 | Wang et al. | |
| 2014/0316032 | A1 * | 10/2014 | Xalter | C08K 5/5399 523/452 |

FOREIGN PATENT DOCUMENTS

| | | | | |
|---|---|---|---|---|
| CN | 1738678 | A | 2/2006 | |
| CN | 1741849 | A | 3/2006 | |
| CN | 101052605 | A | 10/2007 | |
| CN | 103285926 | A * | 9/2013 | ............ B01J 31/24 |
| EP | 2987783 | A1 | 2/2016 | |
| KR | 20150058049 | A | 5/2015 | |
| WO | 2006108803 | A1 | 10/2006 | |
| WO | 2007057455 | A1 | 5/2007 | |
| WO | 2008014139 | A2 | 1/2008 | |
| WO | 2013068437 | A2 | 5/2013 | |
| WO | WO 2013/068437 | A2 * | 5/2013 | ........... C08K 5/5399 |

OTHER PUBLICATIONS

International Search Report from PCT/KR2014/011078, dated Feb. 10, 2015.
Written Opinion of the ISA from PCT/KR2014/011078, dated Feb. 10, 2015.
Kevin Blann, et al., "Ethylene tetramerisation: Subtle effects exhibited by N-substituted diphosphinoamine ligands", Journal of Catalysis, 249 (2007) 244-249.
Annette Bollman,et al., "Ethylene Tetramerization: A New Route to Produce 1-Octene in Exceptionally High Selectivities", J. Am. Chem. Soc., 2004, 126, 14712-14713.
Anthea Carter, et al., "High activity ethylene trimerisation catalysts based on diphosphine ligands", Chem. Commun., 2002, 858-859.
Tao Jiang, et al., "Ethylene tetramerization with a highy active and long-lifetime trinuclear diphenylphosphinoamine/Cr(III)/MAO catalyst", Chin. Sci. Bull., May 2012 vol. 57 No. 13: 1510-1515.
Sven Kuhlmann, et al., "N-substituted diphosphinoamines: Toward rational ligand design for the efficient tetramerization of ethylene" Journal of Catalysis 245 (2007) 279-284.
David S. McGuinness, "Olefin Oligomerization via Metallacycles: Dimerization, Trimerization, Tetramerization, and Beyond", Chem. Rev. 2011, 111, 2321-2341.

* cited by examiner

*Primary Examiner* — Rip A Lee
(74) *Attorney, Agent, or Firm* — Dentons US LLP

(57) ABSTRACT

The present invention relates to a compound represented by Chemical Formula 1, a catalyst system for olefin oligomerization comprising the same, and a method of olefin oligomerization using the same.

14 Claims, No Drawings

CATALYST SYSTEM FOR OLEFIN OLIGOMERIZATION, AND METHOD FOR OLEFIN OLIGOMERIZATION USING THE SAME

This application is a National Stage Application of International Application No. PCT/KR2014/011078, filed Nov. 18, 2014, and claims the benefit of Korean Application No. 10-2013-0139995, filed Nov. 18, 2013, and Korean Application No. 10-2014-0160180, filed Nov. 17, 2014, all of which are hereby incorporated by reference in their entirety for all purposes as if fully set forth herein.

TECHNICAL FIELD

The present invention relates to a ligand compound, a catalyst system for olefin oligomerization, and a method for olefin oligomerization using the same.

BACKGROUND

A linear alpha-olefin, which is an important material used for a comonomer, a cleaner, a lubricant, a plasticizer, and the like, is commercially widely used, and particularly, 1-hexene and 1-octene are used a lot as a comonomer for controlling the density of polyethylene when preparing linear low-density polyethylene (LLDPE).

In the existing preparation process of LLDPE, ethylene is copolymerized with alpha-olefin comonomers such as 1-hexene and 1-octene, so as to form a branch in a polymer backbone to control the density thereof.

Thus, there is a problem in that the cost of comonomers accounts for a large part of the production cost in the preparation of LLPDE having a high comonomer content. There have been various attempts to solve the problem.

Further, since alpha-olefins have a different application field or market size according to the kind, a technology for selectively producing specific olefins is commercially very important, and recently, many studies have been carried out on a chromium catalyst technology for preparing 1-hexene or 1-octene with high selectivity through selective ethylene oligomerization.

The existing commercial preparation methods of 1-hexene or 1-octene include a SHOP process of Shell Chemical, a Ziegler process of Chevron Philips, and the like, whereby $C_{4-20}$ alpha-olefins with wide distributions can be produced.

As a catalyst for trimerization of ethylene, a chromium-based catalyst using a ligand of a General Formula (R1)(R2)X-Y-X(R3)(R4) has been suggested. In the formula, X is phosphorous, arsenic, or antimony, Y is a linking group such as —N(R5)—, and at least one of R1, R2, R3, and R4 has a polar or electron donating substituent.

Further, as a ligand that does not exhibit catalytic activity to 1-hexene under a catalytic condition, studies have been carried out on (o-ethylphenyl)$_2$PN(Me)P(o-ethylphenyl)$_2$, which does not have a polar substituent on at least one of R1, R2, R3, and R4 (*Chem. Commun.*, 2002, 858).

However, regarding the above-explained ligand containing a heteroatom of the prior art, there is continued demand for consistently continued multimerization activity and high selectivity when preparing 1-octene or 1-hexene.

PRIOR ART

Non-Patent Art

1. *Chem. Commun.*, 2002, 858

DISCLOSURE

Technical Problem

It is an object of the present invention to provide a novel ligand compound that can oligomerize olefins with high catalytic activity and selectivity, a catalyst system for olefin oligomerization comprising the same, and a method for olefin oligomerization using the same.

Technical Solution

The present invention provides a compound represented by the following Chemical Formula 1.

[Chemical Formula 1]

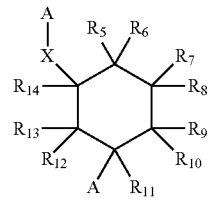

In Chemical Formula 1,
A is represented by the following Chemical Formula 2,

[Chemical Formula 2]

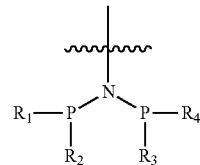

wherein X is a $C_{1-20}$ alkylene or a $C_{6-14}$ arylene, $R_1$ to $R_4$ are independently a $C_{1-20}$ alkyl, a $C_{2-20}$ alkenyl, a $C_{6-14}$ aryl, a $C_{6-14}$ aryl substituted with a $C_{1-4}$ alkyl, a $C_{1-4}$ alkyl substituted with a $C_{6-14}$ aryl, or a $C_{6-14}$ aryl substituted with a $C_{1-4}$ alkoxy, and $R_5$ to $R_{14}$ are independently hydrogen, a $C_{1-20}$ alkyl, a $C_{2-20}$ alkenyl, a $C_{6-14}$ aryl, a $C_{6-14}$ aryl substituted with a $C_{1-4}$ alkyl, a $C_{1-4}$ alkyl substituted with a $C_{6-14}$ aryl, or a $C_{6-14}$ aryl substituted with a $C_{1-4}$ alkoxy.

Preferably, X is methylene or phenylene.

Further, preferably, $R_1$ to $R_4$ are identical to each other. More preferably, $R_1$ to $R_4$ are phenyl.

Further, preferably, $R_5$ and $R_6$ are hydrogen.

Further, preferably, $R_7$ and $R_8$ are identical to each other, and are hydrogen or methyl.

Further, preferably, $R_9$ is hydrogen or iso-propyl. And preferably, $R_{10}$ is hydrogen.

Further, preferably, $R_{11}$ to $R_{13}$ are hydrogen.

Further, preferably, $R_{14}$ is hydrogen or methyl.

Further, preferably, X is methylene or phenylene, $R_1$ to $R_4$ are phenyl, $R_5$ and $R_6$ are hydrogen, $R_7$ and $R_8$ are identical to each other and are hydrogen or methyl, $R_9$ is hydrogen or iso-propyl, $R_{10}$ to $R_{13}$ are hydrogen, and $R_{14}$ is hydrogen or methyl.

Representative examples of the compound represented by Chemical Formula 1 are as follows:

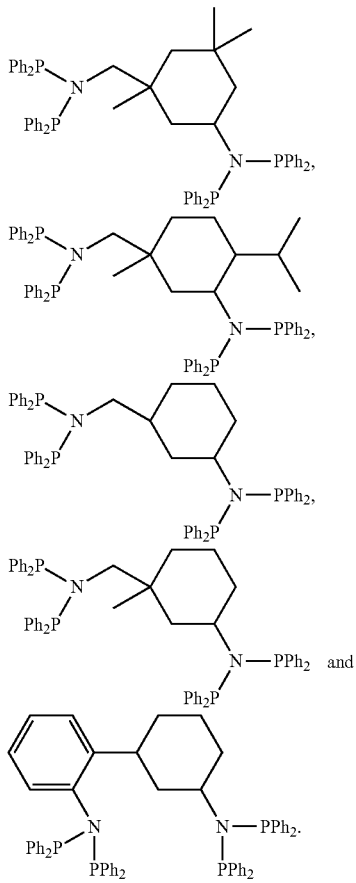

The compound represented by Chemical Formula 1 includes all possible optical isomers.

Further, the present invention provides a method for preparing a compound represented by Chemical Formula 1 as shown in the following Reaction Formula 1.

[Reaction Formula 1]

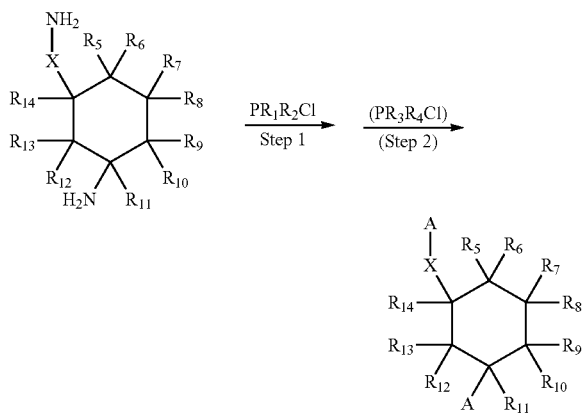

In the Reaction Formula 1, A, X, and $R_5$ to $R_{14}$ are as defined above.

The step 1 is a reaction for substituting an amine group of a starting material with an A substituent, wherein the starting material and $PR_1R_2Cl$ are reacted. It is preferable that trimethylamines are reacted together, and that dichloromethane is used as a solvent.

If the structure of $R_1$ and $R_2$ ($PR_1R_2$) of the substituent A is identical to the structure of $R_3$ and $R_4$ ($PR_3R_4$), a compound of Chemical Formula 1 may be prepared by the step 1. If the structure of $R_1$ and $R_2$ ($PR_1R_2$) of the substituent A is different from the structure of $R_3$ and $R_4$ ($P R_3R_4$), the step 2 is conducted to prepare a compound represented by Chemical Formula 1. The step 2 is identical to the step 1, except using $PR_3R_4Cl$ as a reactant.

Further, the present invention provides a catalyst system for olefin oligomerization, comprising the compound represented by Chemical Formula 1, a source of a transition metal, and a cocatalyst.

As used herein, the term 'olefin oligomerization' means polymerization of a small number of olefins. When three olefins are polymerized, it is referred to as trimerization, when four olefins are polymerized, it is referred to as tetramerization, and the process of polymerization of a small number of olefins to form low molecular weight material is generally referred to as multimerization. Particularly, in the present invention, selective preparation of 1-hexene and 1-octene, main comonomers of LLDPE, from ethylene, is referred to.

Selective olefin oligomerization is closely related to a catalyst system used. A catalyst system used for olefin oligomerization comprises a source of a transition metal functioning as a main catalyst, and a cocatalyst, wherein the structure of the active catalyst may be changed according to the chemical structure of a ligand, thereby varying olefin selectivity and activity.

Thus, the catalyst system for olefin oligomerization according to the present invention uses a compound represented by Chemical Formula 1 as a ligand, to selectively prepare 1-hexene and 1-octene. Without being bound by any theory, it is judged that the compound represented by Chemical Formula 1 has two substituents A that can be coordinated to a main catalyst, has a structure wherein the substituents A in the compound are connected to a linker of a cyclohexane-X structure, and due to the flexible linker, two A substituents, which are active sites where oligomerization occurs, effectively interact to increase activity and selectivity of the catalyst.

The source of the transition metal functions as a main catalyst, and preferably, is at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III) acetate hydroxide.

The cocatalyst is an organic metal compound including a Group 13 metal, and is not specifically limited as long as it can be used for olefin multimerization in the presence of a transition metal catalyst. Specifically, as the cocatalyst, at least one selected from the group consisting of the compounds represented by the following Chemical Formulae 3 to 5 may be used.

$$-[Al(R_{15})-O]_c-$$  [Chemical Formula 3]

In Chemical Formula 3, $R_{15}$'s are independently a halogen, a $C_{1-20}$ alkyl, or a $C_{1-20}$ haloalkyl, and c is an integer equal to or greater than 2.

$$D(R_{16})_3 \qquad \text{[Chemical Formula 4]}$$

In Chemical Formula 4,

D is aluminum or boron, $R_{16}$ is a $C_{1-20}$ alkyl or a $C_{1-20}$ haloalkyl.

$$[L-H]^+[Q(E)_4]^- \qquad \text{[Chemical Formula 5]}$$

In Chemical Formula 5,

L is a neutral Lewis base, $[L-H]^+$ is a Bronsted acid,

Q is $Br^{3+}$ or $Al^{3+}$, and

E's are independently a $C_{6-20}$ aryl or a $C_{1-20}$ alkyl, wherein the $C_{6-20}$ aryl or $C_{1-20}$ alkyl is unsubstituted or substituted with at least one substituent selected from the group consisting of a halogen, a $C_{1-20}$ alkyl, a $C_{1-20}$ alkoxy, and a phenoxy.

Examples of the compound represented by Chemical Formula 3 may include methylaluminoxane (MAO), ethylaluminoxane, isobutylaluminoxane, or butylaluminoxane.

Examples of the compound represented by Chemical Formula 4 may include trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tollylaluminum, dimethylaluminummethoxide, dimethylaluminumethoxide, trimethylboron, triethylboron, triisobutylboron, tripropylboron or tributylboron.

Examples of the compound represented by Chemical Formula 5 may include triethylammonium tetraphenylboron, tributylammonium tetraphenylboron, trimethylammonium tetraphenylboron, tripropylammonium tetraphenylboron, trimethylammonium tetra(p-tolyl)boron, tripropylammonium tetra(p-tollyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tollyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylboron, triphenylcarbonium tetraphenylaluminum, triphenylcarbonium tetra(p-trifluoromethylphenyl)boron, or triphenylcarbonium tetrapentafluorophenylboron.

The catalyst system for olefin oligomerization according to the present invention may have a mole ratio of the compound represented by Chemical Formula 1:source of transition metal:cocatalyst of about 1:1:1 to about 10:1:10,000, preferably about 1:1:100 to about 5:1:3,000, so as to increase selectivity to linear alpha-olefin and multimerization activity.

In the catalyst system for olefin oligomerization comprising the compound represented by Chemical Formula 1, a source of the transition metal, and the cocatalyst, the three components may be added simultaneously or sequentially in a random order in a suitable solvent in the absence or presence of monomers, and be obtained as an active catalyst. The active solvent may include heptane, toluene, 1-hexene, diethylether, tetrahydrofuran, acetonitrile, dichloromethane, chloroform, chlorobenzene, methanol, acetone, and the like, but is not limited thereto.

The present invention also provides a method for preparation of olefin oligomer, comprising the step of multimerizing olefins in the presence of the catalyst system for olefin oligomerization. If the catalyst system for olefin oligomerization according to the present invention is used, a method for olefin oligomerization with improved activity and selectivity may be provided. The olefin may preferably be ethylene.

The olefin oligomerization according to the present invention may be conducted as a homogeneous liquid phase reaction, a slurry reaction wherein a catalyst system is not dissolved in part or in whole, a two-phase liquid/liquid reaction, or a bulk phase reaction or a gas phase reaction wherein a product olefin acts as a main medium, in the absence or presence of an inert solvent, using the catalyst system for olefin oligomerization and a common device and contact technology, and the homogeneous liquid phase reaction is preferable.

The olefin oligomerization may be conducted in any inert solvent that does not react with a catalyst compound and an activator. The suitable inert solvent may include benzene, toluene, xylene, cumene, heptane, cyclohexane, methylcyclohexane, methylcyclopentane, hexane, pentane, butane, isobutane, and the like, but is not limited thereto. Herein, the solvent may be treated with a small amount of alkylaluminum to remove a small amount of water or air acting as a catalyst poison, before use.

The olefin oligomerization may be conducted at a temperature of about 5° C. to about 200° C., preferably about 30° C. to about 150° C. Further, the olefin oligomerization may be conducted at a pressure of about 1 bar to about 300 bar, preferably about 2 bar to about 150 bar.

According to examples of the invention, it was confirmed that as a result of oligomerizing ethyne with a catalyst system using the compound represented by Chemical Formula 1 as a ligand, 1-hexene and 1-octene are selectively synthesized.

Advantageous Effects

By using a compound represented by Chemical Formula 1 according to the present invention and a catalyst system comprising the same, an olefin may be oligomerized with higher catalytic activity and selectivity compared to the existing catalyst system.

EXAMPLES

Hereinafter, the present invention will be explained in detail with reference to the following examples. However, these examples are only to illustrate the invention, and the scope of the invention is not limited thereto.

All the reactions were progressed using a Schlenk technique or a glove box under an argon atmosphere. The synthesized compounds were analyzed by $^1$H(500 MHz) and $^{31}$P(202 MHz) NMR spectra using a Varian 500 MHz spectrometer. Shift was expressed in ppm, downfield from TMS, with a residual solvent peak as a reference. A phosphorous probe was calibrated with aqueous $H_3PO_4$.

Example 1

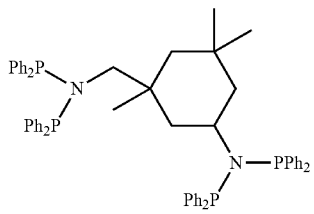

Under an argon atmosphere, 5-amino-1,3,3-trimethylcyclohexanemethylamine (5 mmol) and triethylamine (3~10 equivalents) were dissolved in dichloromethane (80 mL). While the flask was immersed in a water bath, chlorodiphenylphosphine (20 mmol) was slowly added, and the mixture was stirred overnight. The solvent was removed under vacuum, and then THF was added, the mixture was sufficiently stirred, and triethylammonium chloride salt was removed with an air-free glass filter. The solvent was removed from the filtrate to obtain a target compound.

$^{31}$P NMR: 45.6 (br s), 56.2 (br s)

Comparative Example 1

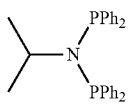

A target compound was prepared by the same method as Example 1, except using 2-aminopropane (10 mmol) instead of 5-amino-1,3,3-trimethylcyclohexanemethyhlamine.

$^{31}$P NMR: 48.4 (br s)

Experimental Example 1

Step 1

Under argon gas, Cr(acac)$_3$ (17.5 mg, 0.05 mmol) and the compound prepared in the Example (0.025 mmol) were added into a flask, cyclohexane (10 mL) was added, and the mixture was stirred to prepare a 5 mM solution.

Step 2

A 600 mL Parr reactor was prepared, vacuum was applied at 120° C. for 2 hours, the internal atmosphere was then replaced with argon, and the temperature was decreased to 45° C. Cyclohexane (270 g) and 2 mL of MMAO (isoheptane solution, Al/Cr=300) were added, and 2 mL of the 5 mM solution (10 μmol) was added into the reactor. The mixture was stirred at 500 rpm for 2 minutes, a valve of an ethylene line adjusted to 45 bar was opened to fill the inside of the reactor with ethylene, and the mixture was stirred at 500 rpm for 15 minutes. The ethylene line valve then was closed, the reactor was cooled to 0° C. with a dry ice/acetone bath, non-reacted ethylene was slowly vented, and 0.5 mL of nonane (GC internal standard) was added. After stirring for 10 seconds, 2 mL of the liquid part of the reactor was taken and quenched with water, and the organic part was filtered with a PTFE syringe filter to make a GC sample. The GC sample was analyzed with GC.

Step 3

400 mL of ethanol/HCl (10 vol %) was added to the remaining reaction solution, and the mixture was stirred and filtered to obtain a polymer. The obtained polymer was dried overnight in a vacuum oven at 65° C., and the weight was measured.

Experimental Example 2

The same process as Experimental Example 1 was conducted, except that in the step 2, 1 mL of the MMAO (isoheptane solution, Al/Cr=300) was used instead of 2 mL, and that 1 mL (5 μmol) of the 5 mM solution was used instead of 2 mL (10 μmol).

Experimental Example 3

The same process as Experimental Example 1 was conducted, except that in the step 2, 4 mL of MMAO (isoheptane solution, Al/Cr=1200) was used instead of 2 mL of the MMAO (isoheptane solution, Al/Cr=300), and that 1 mL (5 μmol) of the 5 mM solution was used instead of 2 mL (10 μmol).

Experimental Example 4

The same process as Experimental Example 1 was conducted, except that in the step 2, 4 mL of MMAO (isoheptane solution, Al/Cr=1200) was used instead of 2 mL of the MMAO (isoheptane solution, Al/Cr=300), 1 mL (5 μmol) of the 5 mM solution was used instead of 2 mL (10 μmol), and the process was conducted under conditions of ethylene at 60 bar and 60° C. instead of the conditions of ethylene at 45 bar and 45° C.

Experimental Example 5

The same process as Experimental Example 1 was conducted, except that in the step 2, 70 g of cyclohexane was used instead of 270 g, 2 mL of MMAO (isoheptane solution, Al/Cr=1200) was used instead of 2 mL of the MMAO (isoheptane solution, Al/Cr=300), and 0.5 mL (2.5 μmol) of the 5 mM solution was used instead of 2 mL (10 μmol).

Experimental Example 6

The same process as Experimental Example 4 was conducted, except that tris(tetrahydrofuran)chromium trichloride (18.7 mg, 0.05 mmol) was used instead of Cr(acac)$_3$.

Experimental Example 7

The same process as Experimental Example 4 was conducted, except that chromium(III)-2-ethylhexanoate (24.1 mg, 0.05 mmol) was used instead of Cr(acac)$_3$.

Experimental Example 8

The same process as Experimental Example 4 was conducted, except that chromium(III)tris(2,2,6,6-tetramethyl-3,5-heptanedionate) (30.1 mg, 0.05 mmol) was used instead of $Cr(acac)_3$.

Experimental Example 9

The same process as Experimental Example 4 was conducted, except that chromium(III)benzoylacetonate (26.8 mg, 0.05 mmol) was used instead of $Cr(acac)_3$.

Experimental Example 10

The same process as Experimental Example 4 was conducted, except that chromium(III)hexafluoro-2,4-pentanedionate (33.7 mg, 0.05 mmol) was used instead of $Cr(acac)_3$.

Experimental Example 11

The same process as Experimental Example 4 was conducted, except that chromium(III)acetate hydroxide ($Cr_3(CH_3CO_2)_7(OH)_2$, 26.8 mg, 0.05 mmol) was used instead of $Cr(acac)_3$.

Comparative Experimental Example 1

The same process as Experimental Example 1 was conducted, except that in the step 1, the compound prepared in Comparative Example 1 (0.1 mmol) was used instead of the compound prepared in Example 1, and in the step 2, 1 mL of the MMAO (isoheptane solution, Al/Cr=300) was used instead of 2 mL, and 1 mL (5 μmol) of the 5 mM solution was used instead of 2 mL (10 μmol).

Comparative Experimental Example 2

The same process as Experimental Example 1 was conducted, except that in the step 1, the compound prepared in Comparative Example 1 (0.1 mmol) was used instead of the compound prepared in Example 1, and in the step 2, 4 mL of MMAO (isoheptane solution, Al/Cr=1200) was used instead of 2 mL of the MMAO (isoheptane solution, Al/Cr=300), and 1 mL (5 μmol) of the 5 mM solution was used instead of 2 mL (10 μmol).

The results of Experimental Examples 1 to 11 and Comparative Experimental Examples 1 and 2 are shown in the following Table 1.

TABLE 1

| | Poly-ethylene (wt %) | Selectivity (wt %) | | | | Activity (kg/mol/Cr/hr) |
|---|---|---|---|---|---|---|
| | | 1-hexene | 1-octene | 1-$C_{10}$ to 1-$C_{40}$ | Sum | |
| Experimental Example 1 | 0.2 | 18.8 | 63.9 | 7.9 | 90.6 | 22600 |
| Experimental Example 2 | 0.17 | 15.0 | 67.7 | 8.5 | 91.2 | 15700 |
| Experimental Example 3 | 0.03 | 29.5 | 55.2 | 8.7 | 93.4 | 44100 |
| Experimental Example 4 | 0.03 | 24.5 | 59.9 | 7.5 | 91.9 | 46800 |
| Experimental Example 5 | 0.55 | 16.8 | 65.9 | 9.7 | 92.4 | 52500 |
| Experimental Example 6 | 6.05 | 15.9 | 61.5 | 3.3 | 80.7 | 5421 |
| Experimental Example 7 | 0.36 | 17.2 | 67.8 | 6.6 | 91.6 | 20588 |
| Experimental Example 8 | 0.20 | 17.1 | 65.6 | 4.8 | 87.5 | 4742 |
| Experimental Example 9 | 2.60 | 17.4 | 64.7 | 7.2 | 89.3 | 27572 |
| Experimental Example 10 | 3.37 | 20.5 | 38.4 | 2.3 | 61.2 | 475 |
| Experimental Example 11 | 0.0 | 41.2 | 43.5 | 9.6 | 94.3 | 401 |
| Comparative Experimental Example 1 | 0.6 | 12.7 | 67.3 | 6.7 | 86.7 | 1500 |
| Comparative Experimental Example 2 | 0.5 | 11.9 | 68.8 | 5.7 | 86.4 | 4000 |

As shown in the Table 1, it was confirmed that the experimental examples using the compounds according to the present invention exhibit very high multimerization activity compared to the comparative experimental examples, produce very little solid by-products, and have remarkably improved selectivity to alpha-olefins (1-hexene and 1-octene).

The invention claimed is:

1. A catalyst system for olefin oligomerization, comprising a compound represented by the following Chemical Formula 1, a source of a transition metal, and a cocatalyst:

[Chemical Formula 1]

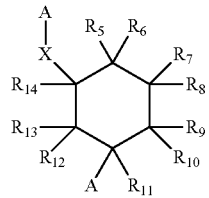

wherein, in Chemical Formula 1,

A is represented by the following Chemical Formula 2,

[Chemical Formula 2]

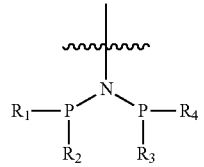

X is a $C_{1-20}$ alkylene or a $C_{6-14}$ arylene, $R_1$ to $R_4$ are independently a $C_{1-20}$ alkyl, a $C_{2-20}$ alkenyl, a $C_{6-14}$ aryl, a $C_{6-14}$ aryl substituted with a $C_{1-4}$ alkyl, a $C_{1-4}$ alkyl substituted with a $C_{6-14}$ aryl, or a $C_{6-14}$ aryl substituted with a $C_{1-4}$ alkoxy, $R_5$ to $R_{14}$ are independently hydrogen, a $C_{1-20}$ alkyl, a $C_{2-20}$ alkenyl, a $C_{6-14}$ aryl, a $C_{6-14}$ aryl substituted with a $C_{1-4}$ alkyl, a $C_{1-4}$ alkyl substituted with a $C_{6-14}$ aryl, or a $C_{6-14}$ aryl substituted with a $C_{1-4}$ alkoxy.

2. The catalyst system according to claim 1, wherein X is methylene or phenylene.

3. The catalyst system according to claim 1, wherein $R_1$ to $R_4$ are identical to each other.

4. The catalyst system according to claim 1, wherein $R_1$ to $R_4$ are phenyl.

5. The catalyst system according to claim 1, wherein $R_5$ and $R_6$ are hydrogen.

6. The catalyst system according to claim 1, wherein $R_7$ and $R_8$ are identical to each other, and are hydrogen or methyl.

7. The catalyst system according to claim 1, wherein $R_9$ is hydrogen or iso-propyl.

8. The catalyst system according to claim 7, wherein $R_{10}$ is hydrogen.

9. The catalyst system according to claim 1, wherein $R_{11}$ to $R_{13}$ are hydrogen.

10. The catalyst system according to claim 1, wherein $R_{14}$ is hydrogen or methyl.

11. The catalyst system according to claim 1, wherein the compound is selected from the group consisting of the following compounds:

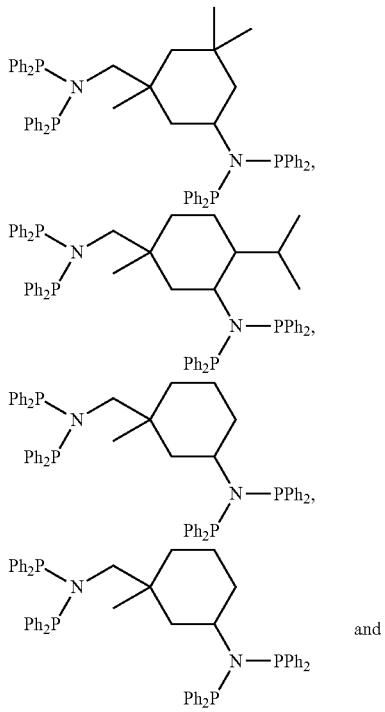

and

-continued

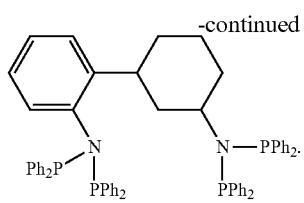

12. The catalyst system according to claim 1, wherein the source of a transition metal is at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III) acetate hydroxide.

13. The catalyst system according to claim 1, wherein the cocatalyst is at least one selected from the group consisting of the compounds represented by the following Chemical Formulae 3 to 5:

$$-[Al(R_{15})-O]_c- \quad \text{[Chemical Formula 3]}$$

in Chemical Formula 3,
$R_{15}$'s are independently a halogen, a $C_{1-20}$ alkyl, or a $C_{1-20}$ haloalkyl, and
c is an integer equal to or greater than 2, $$D(R_{16})_3 \quad \text{[Chemical Formula 4]}$$

in Chemical Formula 4,
D is aluminum or boron, and
$R_{16}$ is a $C_{1-20}$ alkyl or a $C_{1-20}$ haloalkyl, $$[L-H]^+[Q(E)_4]^- \quad \text{[Chemical Formula 5]}$$

in Chemical Formula 5,
L is a neutral Lewis base,
$[L-H]^+$ is a Bronsted acid,
Q is B or Al, and
E's are independently a $C_{6-20}$ aryl or a $C_{1-20}$ alkyl, and are unsubstituted or substituted with at least one substituent selected from the group consisting of a halogen, a $C_{1-20}$ alkyl, a $C_{1-20}$ alkoxy, and a phenoxy.

14. A method for olefin oligomerization, comprising the step of oligomerizing olefins in the presence of the catalyst system for olefin oligomerization according to claim 1.

* * * * *